(12) United States Patent
Kearns, III et al.

(10) Patent No.: US 10,077,421 B2
(45) Date of Patent: Sep. 18, 2018

(54) MEASURING FLOW RATE

(71) Applicant: Terumo BCT, Inc., Lakewood, CO (US)

(72) Inventors: John Kearns, III, Boulder, CO (US); Stanley Liang Chen, Warren, MI (US); Daniel Adam Godrick, Boulder, CO (US); Jon A. Dodd, Littleton, CO (US); Kristina E. Fuerst, Denver, CO (US)

(73) Assignee: Terumo BCT, Inc., Lakewood, CO (US)

( * ) Notice: Subject to any disclaimer, the term of this patent is extended or adjusted under 35 U.S.C. 154(b) by 552 days.

(21) Appl. No.: 14/696,022

(22) Filed: Apr. 24, 2015

(65) Prior Publication Data

US 2015/0307832 A1    Oct. 29, 2015

Related U.S. Application Data

(60) Provisional application No. 61/983,984, filed on Apr. 24, 2014.

(51) Int. Cl.
| | |
|---|---|
| *C12M 1/34* | (2006.01) |
| *C12Q 3/00* | (2006.01) |
| *G01F 1/05* | (2006.01) |
| *G01G 11/06* | (2006.01) |
| *G01G 17/06* | (2006.01) |
| *G01F 9/00* | (2006.01) |
| *G01F 15/00* | (2006.01) |
| *C12M 1/00* | (2006.01) |
| *G01G 19/52* | (2006.01) |

(52) U.S. Cl.
CPC ............ *C12M 41/44* (2013.01); *C12M 29/16* (2013.01); *C12M 41/00* (2013.01); *C12Q 3/00* (2013.01); *G01F 1/05* (2013.01); *G01F 9/003* (2013.01); *G01F 15/001* (2013.01); *G01F 15/003* (2013.01); *G01G 11/06* (2013.01); *G01G 17/06* (2013.01); *G01G 19/52* (2013.01)

(58) Field of Classification Search
CPC ...... C12M 41/44; C12M 41/00; C12M 29/16; C12Q 3/00; G01F 1/05; G01F 9/003; G01F 15/001; G01G 17/06
See application file for complete search history.

(56) References Cited

U.S. PATENT DOCUMENTS

| | | | |
|---|---|---|---|
| 3,821,087 A | 6/1974 | Knazek et al. | |
| 3,896,061 A | 7/1975 | Tanzawa et al. | |
| (Continued) | | | |

FOREIGN PATENT DOCUMENTS

| | | |
|---|---|---|
| EP | 0220650 A2 | 5/1987 |
| JP | H02245177 A | 9/1990 |
| (Continued) | | |

OTHER PUBLICATIONS

Chang et al., "Membrane Bioreactors: Present and Prospects", Advances in Biochemical Engineering, 1991, pp. 27-64, vol. 44.
(Continued)

*Primary Examiner* — Manuel L Barbee
(74) *Attorney, Agent, or Firm* — Terumo BCT, Inc. IP Law Department

(57) ABSTRACT

Embodiments are described that relate to flow rate measuring systems that may be used in cell expansion systems (CES) and in methods for controlling fluid input into systems such as a CES.

7 Claims, 15 Drawing Sheets

(56) References Cited

U.S. PATENT DOCUMENTS

| | | |
|---|---|---|
| 4,391,912 A | 7/1983 | Yoshida et al. |
| 4,439,322 A | 3/1984 | Sonoda et al. |
| 4,647,539 A | 3/1987 | Bach |
| 4,650,766 A | 3/1987 | Harm et al. |
| 4,722,902 A | 2/1988 | Harm et al. |
| 4,804,628 A | 2/1989 | Cracauer et al. |
| 4,885,087 A | 12/1989 | Kopf |
| 4,889,812 A | 12/1989 | Guinn et al. |
| 4,894,342 A | 1/1990 | Guinn et al. |
| 4,918,019 A | 4/1990 | Guinn |
| 4,973,558 A | 11/1990 | Wilson et al. |
| 5,079,168 A | 1/1992 | Amiot |
| 5,126,238 A | 6/1992 | Gebhard et al. |
| 5,162,225 A | 11/1992 | Sager et al. |
| 5,202,254 A | 4/1993 | Amiot |
| 5,330,915 A | 7/1994 | Wilson et al. |
| 5,399,493 A | 3/1995 | Emerson et al. |
| 5,416,022 A | 5/1995 | Amiot |
| 5,437,994 A | 8/1995 | Emerson et al. |
| 5,459,069 A | 10/1995 | Palsson et al. |
| 5,510,257 A | 4/1996 | Sirkar et al. |
| 5,541,105 A | 7/1996 | Melink et al. |
| 5,605,822 A | 2/1997 | Emerson et al. |
| 5,622,857 A | 4/1997 | Goffe |
| 5,631,006 A | 5/1997 | Melink et al. |
| 5,635,386 A | 6/1997 | Palsson et al. |
| 5,635,387 A | 6/1997 | Fei et al. |
| 5,646,043 A | 7/1997 | Emerson et al. |
| 5,656,421 A | 8/1997 | Gebhard et al. |
| 5,670,147 A | 9/1997 | Emerson et al. |
| 5,670,351 A | 9/1997 | Emerson et al. |
| 5,688,687 A | 11/1997 | Palsson et al. |
| 5,709,670 A * | 1/1998 | Vancaillie .......... A61B 5/02042 600/573 |
| 5,763,194 A | 6/1998 | Slowiaczek et al. |
| 5,763,261 A | 6/1998 | Gruenberg |
| 5,763,266 A | 6/1998 | Palsson et al. |
| 5,882,918 A | 3/1999 | Goffe |
| 5,888,807 A | 3/1999 | Palsson et al. |
| 5,958,763 A | 9/1999 | Goffe |
| 5,981,211 A | 11/1999 | Hu et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,048,721 A | 4/2000 | Armstrong et al. |
| 6,096,532 A | 8/2000 | Armstrong et al. |
| 6,228,635 B1 | 5/2001 | Armstrong et al. |
| 6,238,908 B1 | 5/2001 | Armstrong et al. |
| 6,326,198 B1 | 12/2001 | Emerson et al. |
| 6,566,126 B2 | 5/2003 | Cadwell |
| 6,582,955 B2 | 6/2003 | Martinez et al. |
| 6,616,912 B2 | 9/2003 | Eddleman et al. |
| 6,642,019 B1 | 11/2003 | Anderson et al. |
| 6,667,034 B2 | 12/2003 | Palsson et al. |
| 6,835,566 B2 | 12/2004 | Smith et al. |
| 6,844,187 B1 | 1/2005 | Weschler et al. |
| 6,943,008 B1 | 9/2005 | Ma |
| 6,969,308 B2 | 11/2005 | Doi et al. |
| 6,979,308 B1 | 12/2005 | McDonald et al. |
| 7,033,823 B2 | 4/2006 | Chang |
| 7,041,493 B2 | 5/2006 | Rao |
| 7,112,441 B2 | 9/2006 | Uemura et al. |
| 7,172,696 B1 | 2/2007 | Martinez et al. |
| 7,270,996 B2 | 9/2007 | Cannon et al. |
| 7,531,351 B2 | 5/2009 | Marx et al. |
| 7,682,822 B2 | 3/2010 | Noll et al. |
| 7,718,430 B2 | 5/2010 | Antwiler |
| 8,309,347 B2 | 11/2012 | Antwiler |
| 8,785,181 B2 | 7/2014 | Antwiler |
| 9,260,698 B2 | 2/2016 | Antwiler |
| 2006/0233834 A1 | 10/2006 | Guehenneux et al. |
| 2007/0122904 A1 | 5/2007 | Nordon |
| 2007/0160583 A1 | 7/2007 | Lange et al. |
| 2007/0298497 A1 | 12/2007 | Antwiler |
| 2008/0220522 A1 | 9/2008 | Antwiler |
| 2008/0227190 A1 | 9/2008 | Antwiler |
| 2008/0248572 A1 | 10/2008 | Antwiler |
| 2008/0254533 A1 | 10/2008 | Antwiler |
| 2011/0206646 A1 * | 8/2011 | Alfonso .................. A61K 35/28 424/93.7 |
| 2015/0017711 A1 * | 1/2015 | Bennett .................. C12M 23/50 435/286.2 |

FOREIGN PATENT DOCUMENTS

| | | |
|---|---|---|
| JP | 2003510068 | 3/2003 |
| JP | 2005278564 A | 10/2005 |
| JP | 2007000038 A | 1/2007 |
| WO | 86/02379 A1 | 4/1986 |
| WO | 88/01643 A1 | 3/1988 |
| WO | 90/02171 A1 | 3/1990 |
| WO | 91/07485 A1 | 5/1991 |
| WO | 92/10564 A1 | 6/1992 |
| WO | 95/04813 A1 | 2/1995 |
| WO | 95/21911 A1 | 8/1995 |
| WO | 97/16527 A1 | 5/1997 |
| WO | 98/53046 A1 | 11/1998 |
| WO | 00/75275 A2 | 12/2000 |
| WO | 01/23520 A1 | 4/2001 |
| WO | 02/28996 A1 | 4/2002 |
| WO | 03/105663 A2 | 12/2003 |
| WO | 2004/090112 A2 | 10/2004 |
| WO | 2005087915 A2 | 9/2005 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A2 | 12/2007 |
| WO | 2008109674 A2 | 9/2008 |
| WO | WO 2008109674 A2 * | 9/2008 ............ C12M 25/10 |
| WO | 2013116421 A1 | 8/2013 |

OTHER PUBLICATIONS

Chang, Ho Nam, "Membrane Bioreactors: Engineering Aspects", Biotech. Adv., 1987, pp. 129-145, vol. 5.

Eddington, Stephen M., "New Horizons for Stem-Cell Bioreactors", Biotechnology, Oct. 1992, pp. 1099-1106, vol. 10.

Gastens et al., "Good Manufacturing Practice-Compliant Expansion of Marrow-Derived Stem and Progenitor Cells for Cell Therapy", Cell Transplantation, 2007, pp. 685-696, vol. 16.

Gramer et al., "Screening Tool for Hollow-Fiber Bioreactor Process Development", Biotechnol. Prog., 1998, pp. 203-209, vol. 14.

Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.

Nielsen, Lars Keld, "Bioreactors for Hematopoietic Cell Culture", Annu. Rev. Biomed. Eng., 1999, pp. 129-152, vol. 1.

Portner et al., An overview on Bioreactor Design, Prototyping and Process Control for Reproducible Three-Dimensional Tissue Culture, Drug Testing in Vitro: Breakthroughs and Trends in Cell Culture Technology, ed. Uwe Marx and Volker Sandig, 2007, pp. 53-78, Wiley-VCH.

Zhao et al., "Perfusion Bioreactor System for Human Mesenchymal Stem Cell Tissue Engineering: Dynamic Cell Seeding and Construct Development", Biotechnology and Bioengineering, Aug. 20, 2005, pp. 482-493, vol. 91, No. 4.

International Search Report and Written Opinion, PCT/US2015/027626, dated Aug. 27, 2015.

* cited by examiner

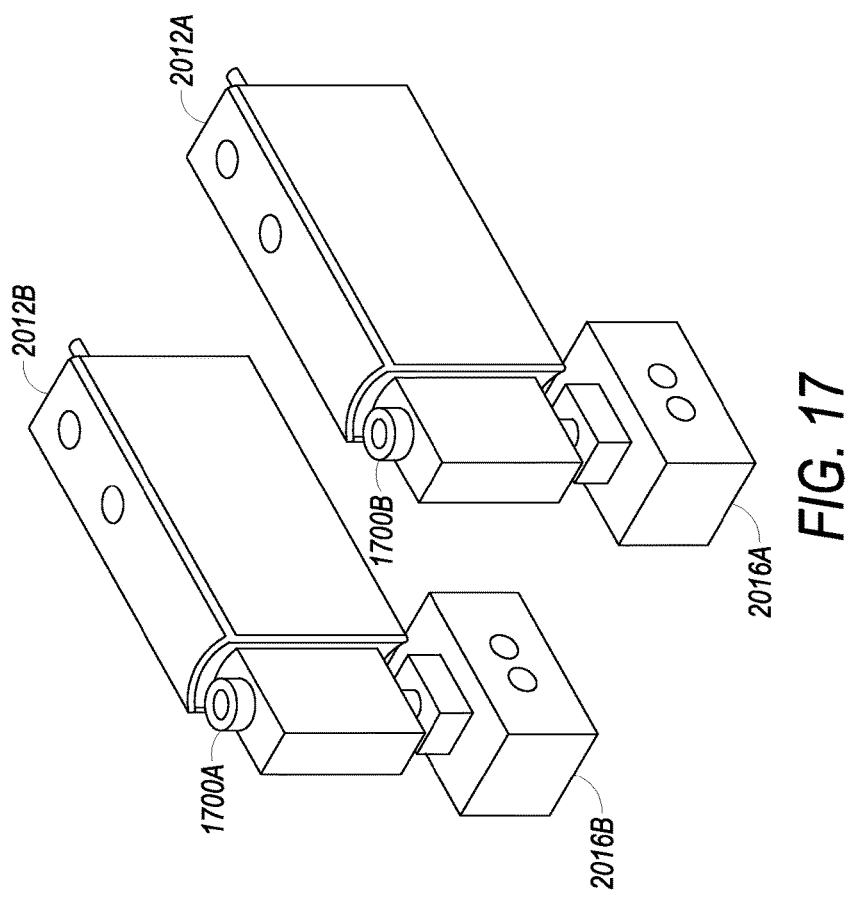

MEASURING FLOW RATE

CROSS-REFERENCE TO RELATED PATENT APPLICATION(S)

This application claims priority to U.S. Provisional Patent Application No. 61/983,984 filed Apr. 24, 2014, and entitled MEASURING FLOW RATE, which is hereby incorporated by reference in its entirety as if set forth herein in full.

BACKGROUND

Having an accurate measure of flow rates may be important in a number of chemical processes and systems, including for example, Cell Expansion Systems (CESs). CESs are used to expand different animal cells types, e.g., mesenchymal stem cells, bone marrow, T cells. CESs utilize different fluids and the growth conditions of a CES may be affected by the flow rates of fluids within the system.

Embodiments have been made in light of these and other considerations. However, the relatively specific problems discussed above do not limit the applicability of the embodiments of the present disclosure.

SUMMARY

The summary is provided to introduce aspects of some embodiments in a simplified form, and is not intended to identify key or essential elements, nor is it intended to limit the scope of the claims.

Embodiments relate to cell expansion systems (CESs) that may include a cell growth chamber and a flow rate measuring system. The flow rate measuring system may include a weight measuring device adapted to weigh a container of fluid and a holding assembly adapted to connect the container of fluid to the weight measurement device. The CES may further include at least one processor, wherein the at least one processor is connected to the flow rate measuring system and may also include a pump connected to the at least one processor and configured to move the fluid from the container into the cell growth chamber.

Embodiments further relate to a flow rate measuring system that may include a holding assembly and at least one weight measuring device. The system may further include a spacer attaching the holding assembly to the weight measuring device and a beam attached to the at least one weight measuring device and adapted to connect to a pole.

Additional embodiments may relate to a method of controlling fluid input into a cell expansion system. The method may include receiving, by a processor, an initial weight of a fluid for pumping into a cell expansion system. The processor may then receive a first pump rate, and a pump may be started at the first pump rate. The processor may then calculate an actual pump rate and determine that the actual pump rate differs from the first pump rate by more than a predetermined amount. In response, the pump may be adjusted based on the determination made by the processor.

BRIEF DESCRIPTION OF THE DRAWINGS

Non-limiting and non-exhaustive embodiments are described with reference to the following figures.

FIGS. 17-20 illustrate an embodiment of assembling a flow rate measuring system according to one embodiment.

DETAILED DESCRIPTION

Figure 1:
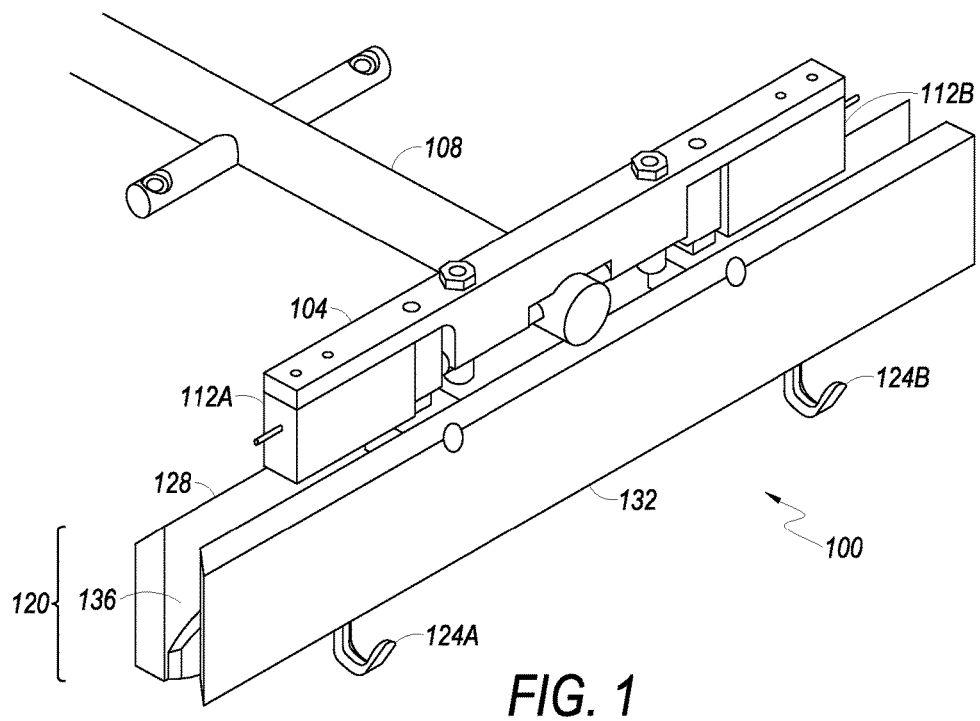
FIG. 1 illustrates a perspective view of a flow rate measuring system according to one embodiment.

The principles of the present disclosure may be further understood by reference to the following detailed description and the embodiments depicted in the accompanying drawings. It should be understood that although specific features are shown and described below with respect to detailed embodiments, the present disclosure is not limited to the embodiments described below.

Reference will now be made in detail to the embodiments illustrated in the accompanying drawings and described below. Wherever possible, the same reference numerals are used in the drawings and the description to refer to the same or like parts.

Figure 2:
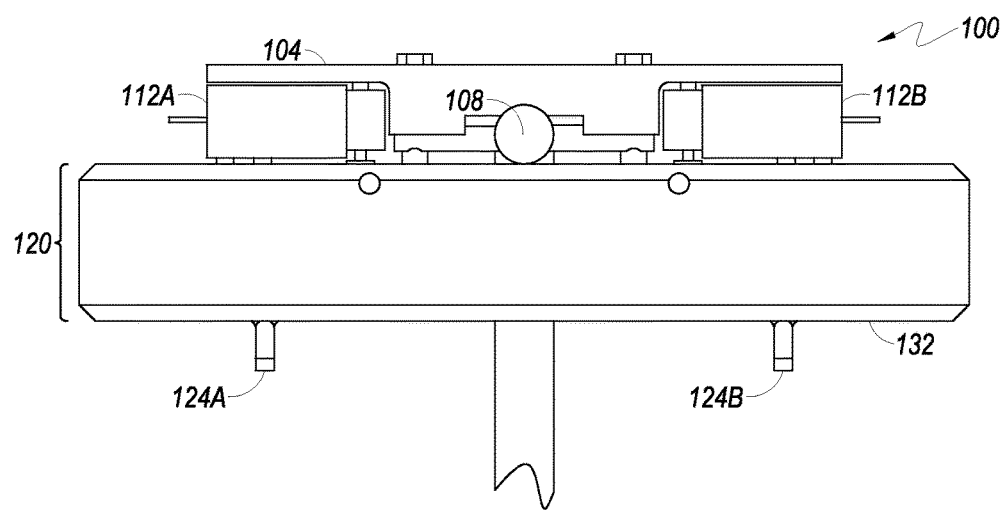
FIG. 2 illustrates a front view of the flow rate measuring system shown in FIG. 1.
Figure 3:
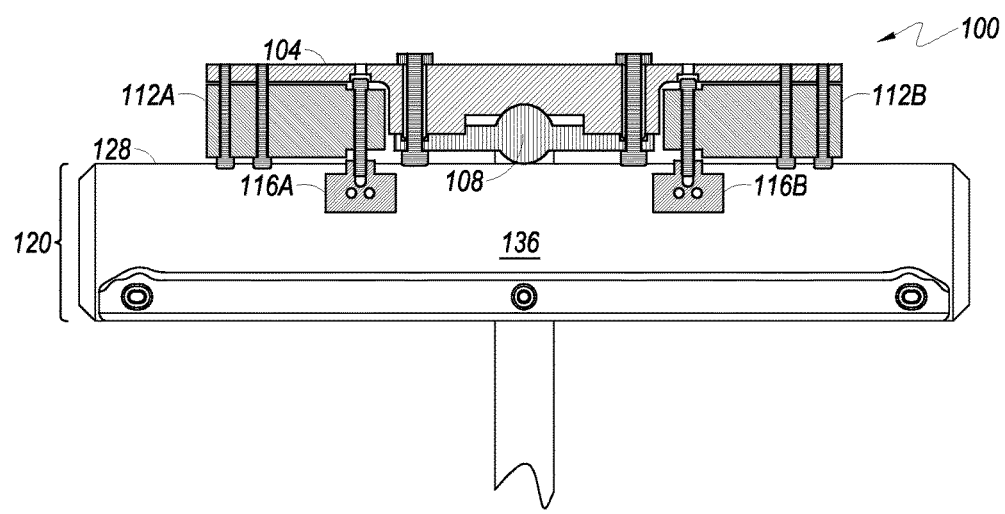
FIG. 3 illustrates a front cross-sectional view of the flow rate measuring system shown in FIGS. 1 and 2.

FIGS. 1 and 2 illustrate different views of a flow rate measuring system 100 according to one embodiment. FIG. 3 illustrates a front cross-sectional view of the flow rate measuring system shown in FIGS. 1 and 2. In the embodiments shown in FIGS. 1-3, flow rate measuring system 100 includes a beam 104 that is adapted to be connected to a pole, such as pole 108, which in embodiments may be a bag pole commonly used for holding bags of fluids. In some embodiments, the beam 104 may be referred to as a tolerance block.

The beam 104 is connected to at least one, e.g., in FIGS. 1-3 there is two, weight measuring devices. In system 100 the weight measuring device(s) are load cells 112A and 112B. One example of load cells that may be used include an Omega LCEB-25 load cell manufactured by Omega Engineering, Stamford, Conn. It is noted that other types of transducers (e.g., combinations of strain gauges) may be used in other embodiments in lieu of or in addition to load cells 112A and 112B.

In the illustrated embodiment, each load cell 112A and 112B is connected to a spacer 116A and 116B respectively. The spacers 116A and 116B are used to connect the load cells 112A and 112B to a holding assembly 120.

The holding assembly 120 includes a number of features and is adapted to hold containers of fluid. For example, in some embodiments, assembly 120 may hold bags of fluid. In these embodiments, hooks 124A and 124B may be used to hold one or more bags of fluid. In addition to hooks 124A and 124B, holding assembly 120 also includes two walls 128 and 132 that form a channel 136. As illustrated in FIGS. 1-3, spacers 116A and 116B are positioned, at least in part, within channel 136.

FIG. 3 illustrates a number of holes that are used to connect various features of system 100 together. In embodiments, a number of different fasteners, some of which may be at least partially positioned in the holes, may be used to connect the features together. Some non-limiting examples of fasteners that may be used include nuts, bolts, screws, washers, pins, anchors, rivets, fittings, etc.

As illustrated in FIG. 3, the load cells 112A and 112B experience the load of any fluid in containers that are connected to assembly 120, because the spacers 116A and 116B are connected to the load cells 112A and 112B and the assembly 120. This allows load cells 112A and 112B to weigh fluid that is stored in containers that are connected to holding assembly 120.

Figure 4:
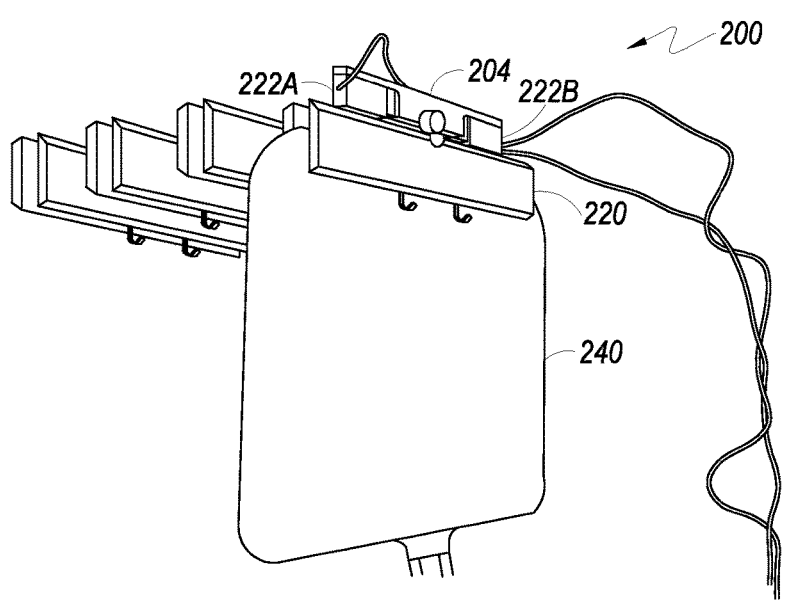
FIG. 4 illustrates a perspective view of a flow rate measuring system according to another embodiment.

FIG. 4 illustrates an embodiment of a flow rate measuring system 200 according to embodiments. FIG. 4 illustrates some parts of system 200 including a beam 204, weight measuring devices 222A and 222B, a holding assembly 220 for holding containers of fluid. In FIG. 4, holding assembly 220 is holding a bag 240 which contains a fluid. Flow rate measuring system 200 can be used to measure the flow rate of a fluid being removed from bag 240, as described in greater detail below.

Figure 5:
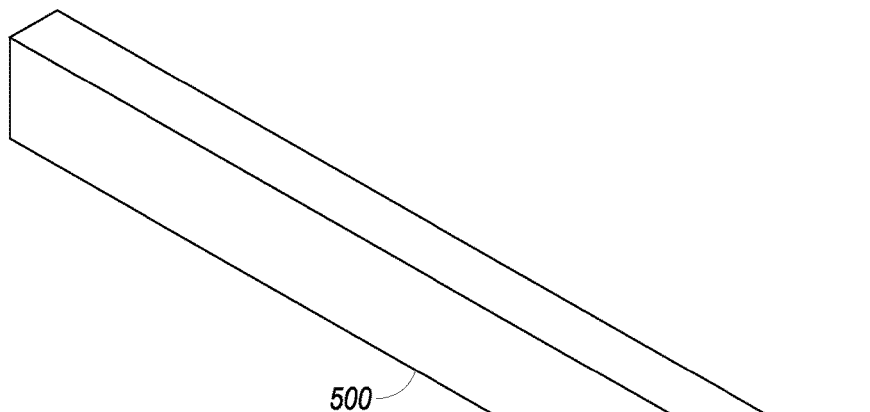
FIGS. 5-12 illustrate a beam, at various stages of manufacturing, for use in a flow rate measuring system such as those illustrated in FIGS. 1-3.

FIGS. 5-12 illustrate a beam, at various stages of manufacturing, for use in a flow rate measuring system such as those illustrated in FIGS. 1-4. FIG. 5 illustrates a block 500 of material. In embodiments, block 500 may be made from a metal such as aluminum. In one specific embodiment, block 500 may be made by first cutting about 8.70" of length from a section of aluminum bar stock of dimensions of about 1" ×about 0.5". The cut section may then be faced with an endmill to obtain a bar section measuring about 8.54" ×about 0.938" ×about 0.50" that may appear as shown in FIG. 5.

Figure 6:
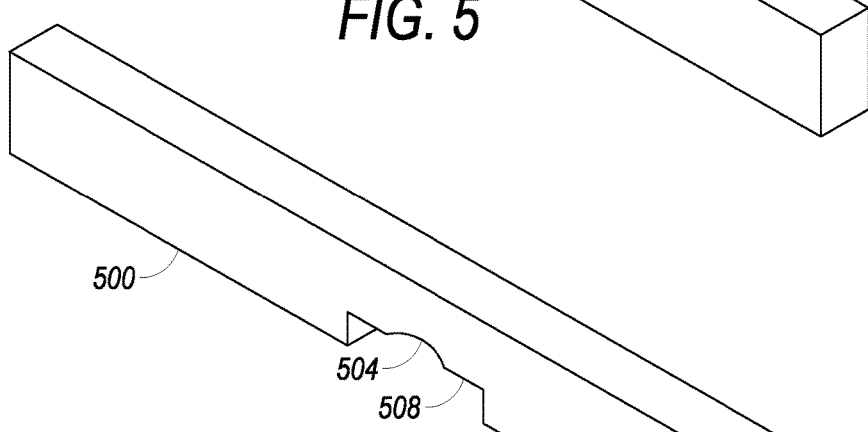

FIG. 6 illustrates block 500 with the addition of a through-hole 504. The through-hole 504 may be created, in some embodiments, with a ¾" ball end mill that cuts through the thickness of the block 500. The through-hole 504 may be centered on the bottom edge and bisect the longitude of block 500. In embodiments, about a ¼"-deep slot 508 may be cut into the same side of the bar that may be about 1¼" long and also may be centered on the through-hole 504.

Figure 7:
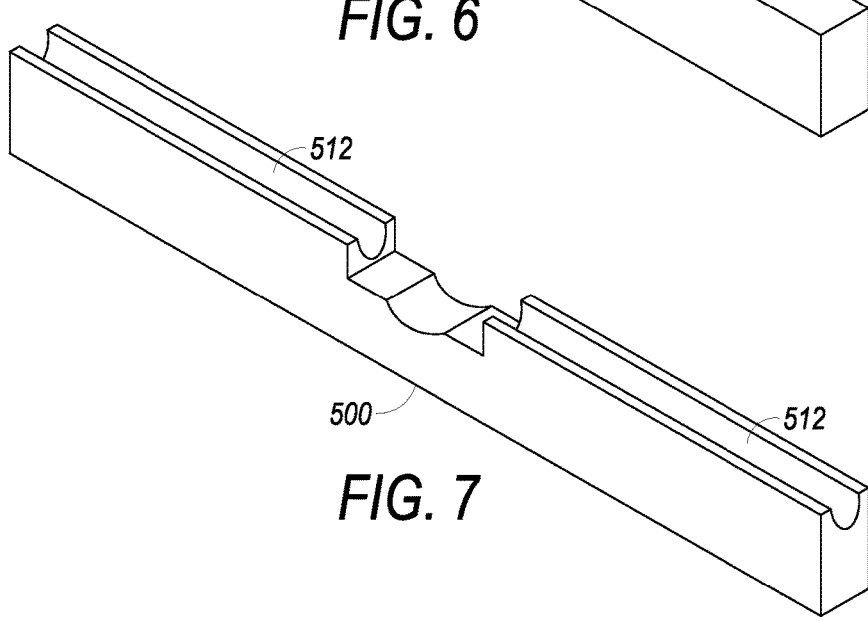

FIG. 7 illustrates block 500 (rotated 180 degrees from FIGS. 5 and 6) with the further addition of a second through-hole 512 (e.g., a channel) along the length of block 500. The second through-hole 512 may be created with a ⅜" ball endmill, cutting along the length of block 500. The second through-hole 512 may be centered on the bottom edge and bisect the thickness of block 500.

Figure 8:
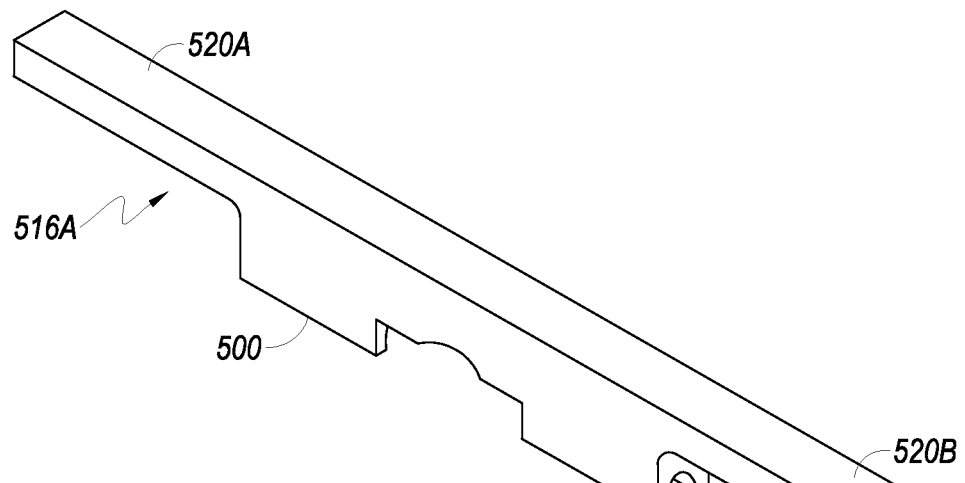

FIG. 8 illustrates block 500 (rotated back 180 degrees to same position as shown in FIGS. 5 and 6) with the further addition of two channels 516A and 516B cut out to create arms 520A and 520B. In embodiments, channels 516A and 516B may be cut with a ⅛" end mill.

Figure 9:
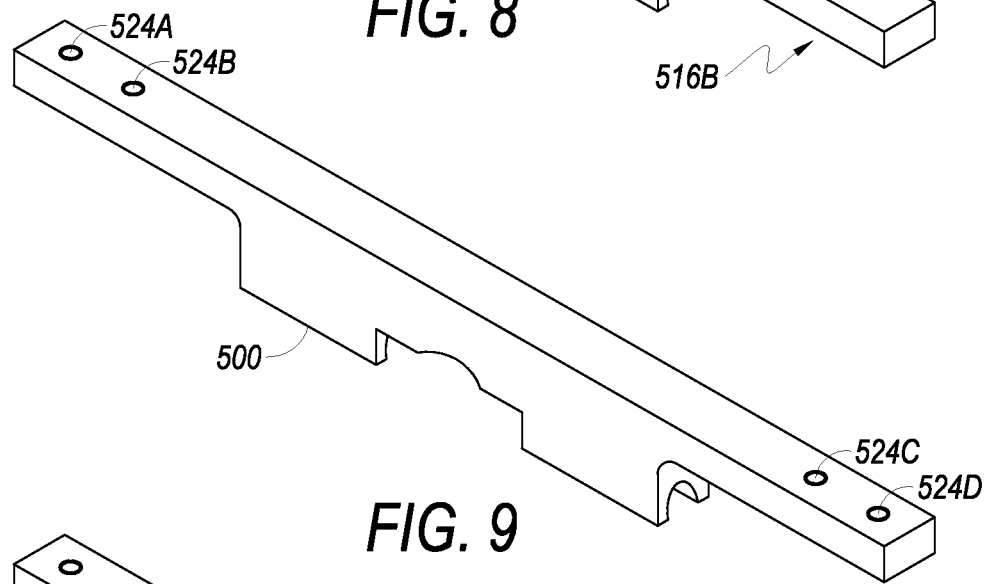

FIG. 9 illustrates block 500 with additional through-holes 524A-D drilled into the arms 520A and 520B. Through-holes 524A-C may be drilled, in some embodiments, using a size 36 clearance drill.

Figure 10:
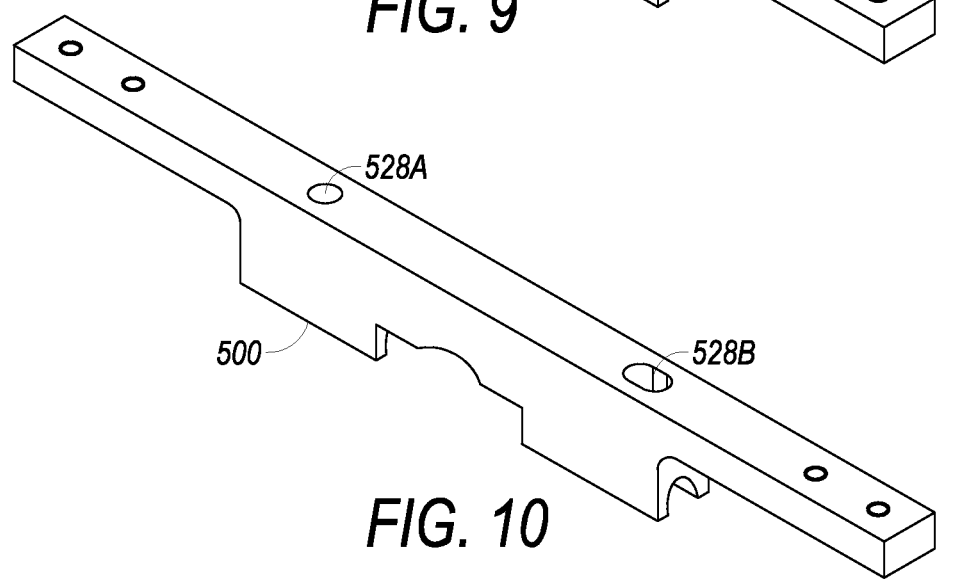

FIG. 10 illustrates block 500 with additional through-holes 528A and 528B drilled into block 500. Through-hole 528A may be drilled, in some embodiments, using a ¹³⁄₆₄" clearance drill. Through-hole 528B may be created using a ¹³⁄₆₄" endmill.

Figure 11:
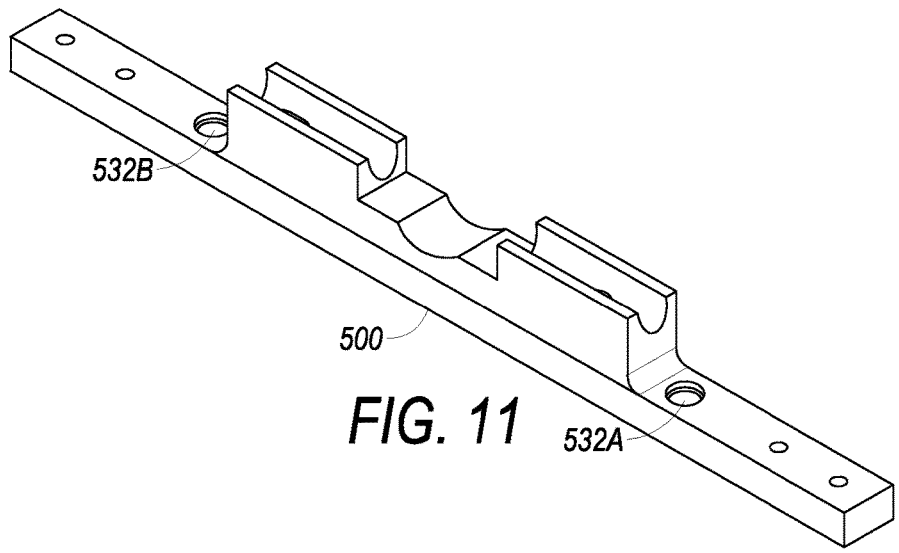

FIG. 11 illustrates block 500 (rotated back 180 degrees to same position as shown in FIG. 7) with the addition of two countersink holes 532A and 532B that may be about 0.1" deep, in some embodiments. In embodiments, counter sink holes 532A and 532B are created with a ¹⁹⁄₆₄" endmill.

Figure 12:
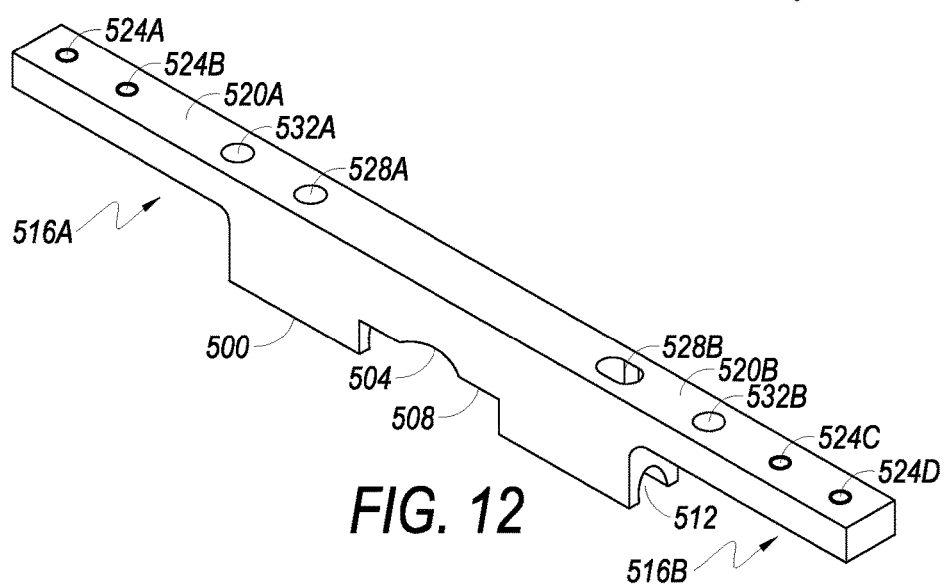

FIG. 12 illustrates block 500 with the addition of threads in the through-holes 524A-D. In embodiments, the threads may be created using a #6-32 hole tap. In embodiments, a deburring tool and/or metal file may be used to deburr edges.

Figure 13:
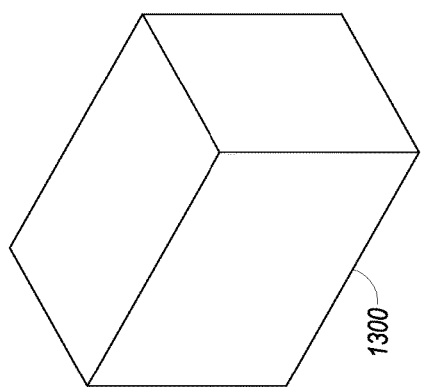

FIGS. 13-16 illustrate a spacer, at various stages of manufacturing, for use in a flow rate measuring system such as those illustrated in FIGS. 1-4. FIG. 13 illustrates a block 1300 of material. In embodiments, block 1300 may be made from a metal such as aluminum. In one specific embodiment, block 1300 is made by cutting about 1.1" of length from a section of aluminum bar stock with dimension of about 0.75" ×about 0.75". In embodiments, the cut section may be faced with an endmill to obtain block 1300 that may have dimension of about 0.92" ×about 0.550" ×about 0.69".

Figure 14:
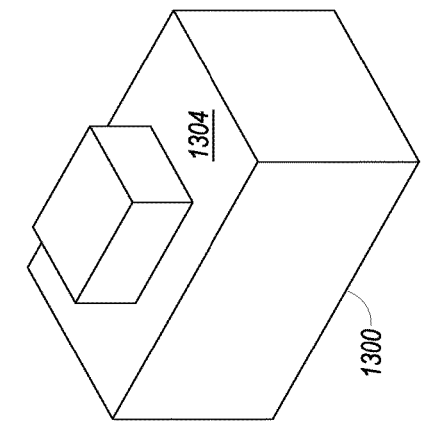
FIGS. 13-16 illustrate a spacer, at various stages of manufacturing, for use in a flow rate measuring system such as those illustrated in FIGS. 1-3.

FIG. 14 illustrates block 1300 with the addition of a channel 1304 around a top portion of block 1300. In embodiments, channel 1304 may be made using an endmill. The channel may be about 0.19" deep from the top face of the block 1300 in some embodiments.

Figure 15:
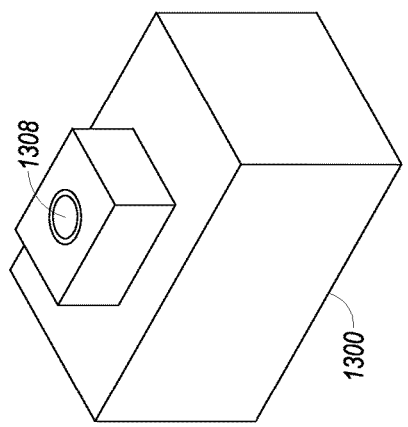

FIG. 15 illustrates block 1300 with the addition of a hole 1308 in the center of block 1300. In embodiments, hole 1308 may be made using a size 36 tap drill, and made to be about 0.3"-deep. In some embodiments, hole 1308 may be threaded with a #6-32 hole tap.

Figure 16:
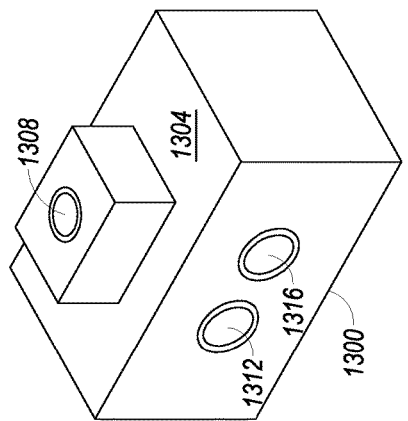

FIG. 16 illustrates block 1300 with the addition of two through-holes 1312 and 1316, which in embodiments may be made using a size 29 tap drill. In embodiments through-holes 1312 and 1316 may be tapped with a #8-32 hole tap. In embodiments, a deburring tool and/or metal file may be used to deburr edges.

FIGS. 17-20 illustrate an embodiment of assembling a flow rate measuring system 2000. As shown in FIG. 17, fasteners 1700A and 1700B (which in embodiments may be #6-32×1" screws) are positioned through a hole in weight measuring devices 2012A and 2012B to connect them each to a spacer 2016A and 2016B respectively. In embodiments, spacers 2016A and 2016B may be manufactured as described above with respect to FIGS. 13-16. The fasteners 1700A and 1700B may be hand tightened to the top hole of each spacer 2016A and 2016B, but with adequate room for a loose fit while ensuring that the threads are still engaged.

Figure 18:
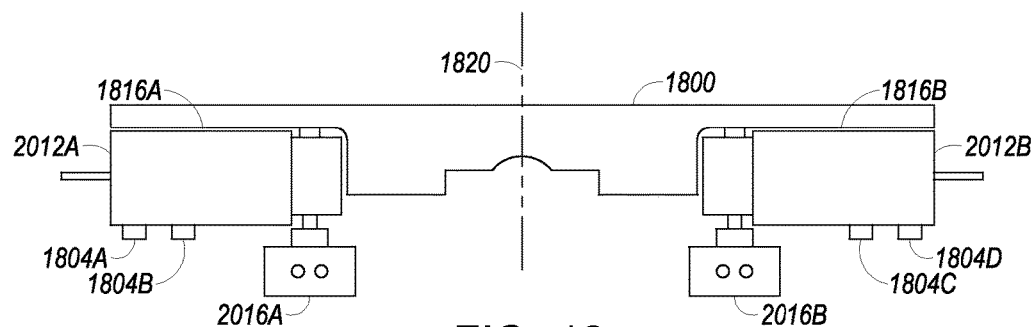

As shown in FIG. 18, a beam 1800 may be connected to the weight measuring devices 2012A and 2012B using fasteners 1804A, 1804B, 1804C, and 1804D (which in embodiments may be, for example, #6-32×1.25" screws). The beam 1800 may in embodiments be manufactured as described above with respect to FIGS. 5-12. In embodiments, the weight measuring devices may be connected on either side of beam 1800.

As shown in FIG. 18 each weight measuring device 2012A and 2012B may be positioned within channels (1816A and 1816B) of beam 1800. For example, device 2012A may be positioned within channel 1816A of beam 1800 and device 2012B may be positioned within channel 1816B of beam 1800. In embodiments, weight measuring devices 2012A and 2012B may be positioned equidistance from a center of beam 1800, which is indicated by line 1820. The position of weight measuring devices 2012A and 2012B may be selected to balance side beam 1800.

Figure 19:
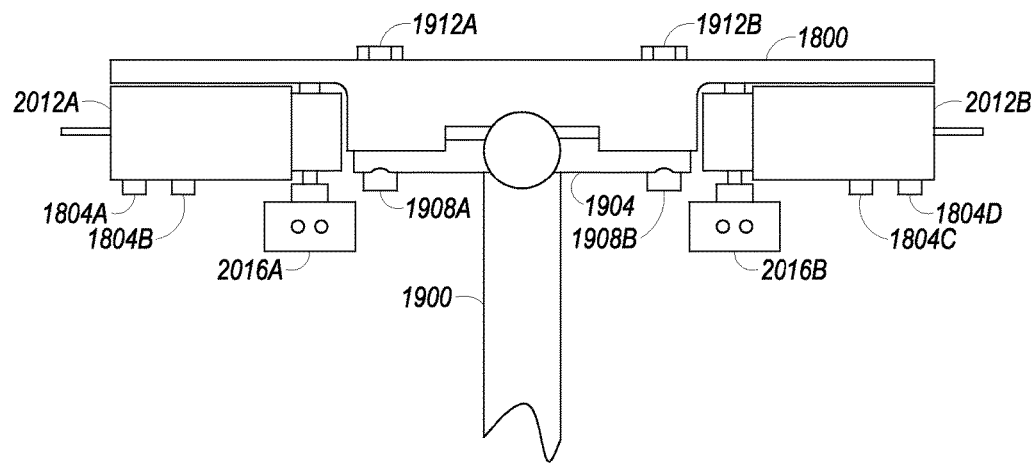

FIG. 19 illustrates the beam 1800 and weight measuring devices 2012A and 2012B connected to a t-junction on a pole 1900. The t-junction may be created by a cross member 1904. Beam 1800 may be connected to cross member 1904 using fasteners 1908A, 1908B, 1912A and 1912B. In one embodiment, fasteners 1908A and 1908B may be screws (e.g., #10-32×1.25") with fasteners 1912A and 1912B being nuts (e.g., #10-32 nuts).

Figure 20:
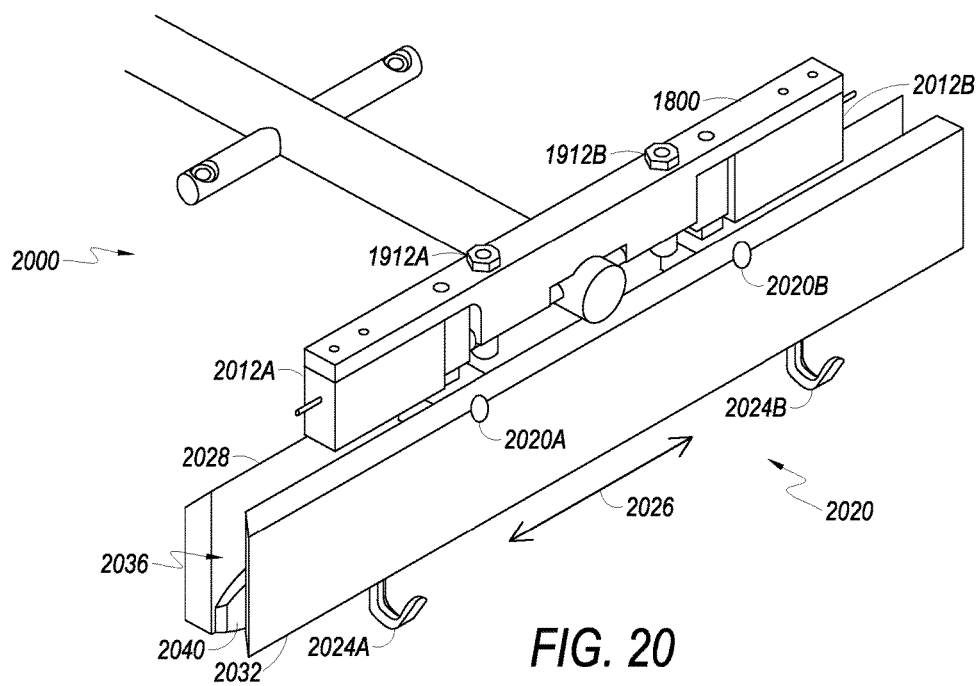

FIG. 20 illustrates a holding assembly 2020 connected to beam 1800 and weight measuring devices 2012A and 2012B. The holding assembly 2020 may be connected to the spacers 2016A and 2016B with fasteners 2020A and 2020B, which may be, e.g., #8-32×0.5" screws in one embodiment. In other embodiments, additional fasteners may be used.

In embodiments, holding assembly 2020 may include the same, or similar, features as holding assembly 120 described above with respect to FIG. 1. Holding assembly 2020 may include features configured to hold containers of fluid. For example, in some embodiments, assembly 2020 may hold bags of fluid. In these embodiments, hooks 2024A and 2024B may be used to hold one or more bags of fluid. In some embodiments, hooks 2024A and 2024B are configured to slide back and forth along the length of the assembly 2020 as shown by arrow 2026 to adjust to the space between holes in a bag. This provides some flexibility on the types of bags that may be held by assembly 2020.

In addition to hooks 2024A and 2024B, holding assembly 2020 includes two walls 2028 and 2032 that form a channel 2036. Spacers 2016A and 2016B may be positioned, at least in part, within channel 2036. Also, in some embodiments, channel 2036 maybe used to hold a bag of fluid. For example, some bags may be held by a member (e.g., plastic member) that extends along a length of a bag. In these embodiments, the member may be slid into channel 2036 through one end of assembly 2020. One or more ridges or lips (e.g., lip 2040) on walls 2028 and/or 2032 may hold the member in channel 2036. As illustrated in FIG. 20, lip 2040 is also within channel 2036. In embodiments, wall 2032 may have a corresponding lip that is opposite lip 2040. The lips together hold a member in channel 2036, which in turn holds a bag of liquid. One example of holding a bag of fluid that may include a member for holding the bag is illustrated in FIG. 4.

Figure 21:
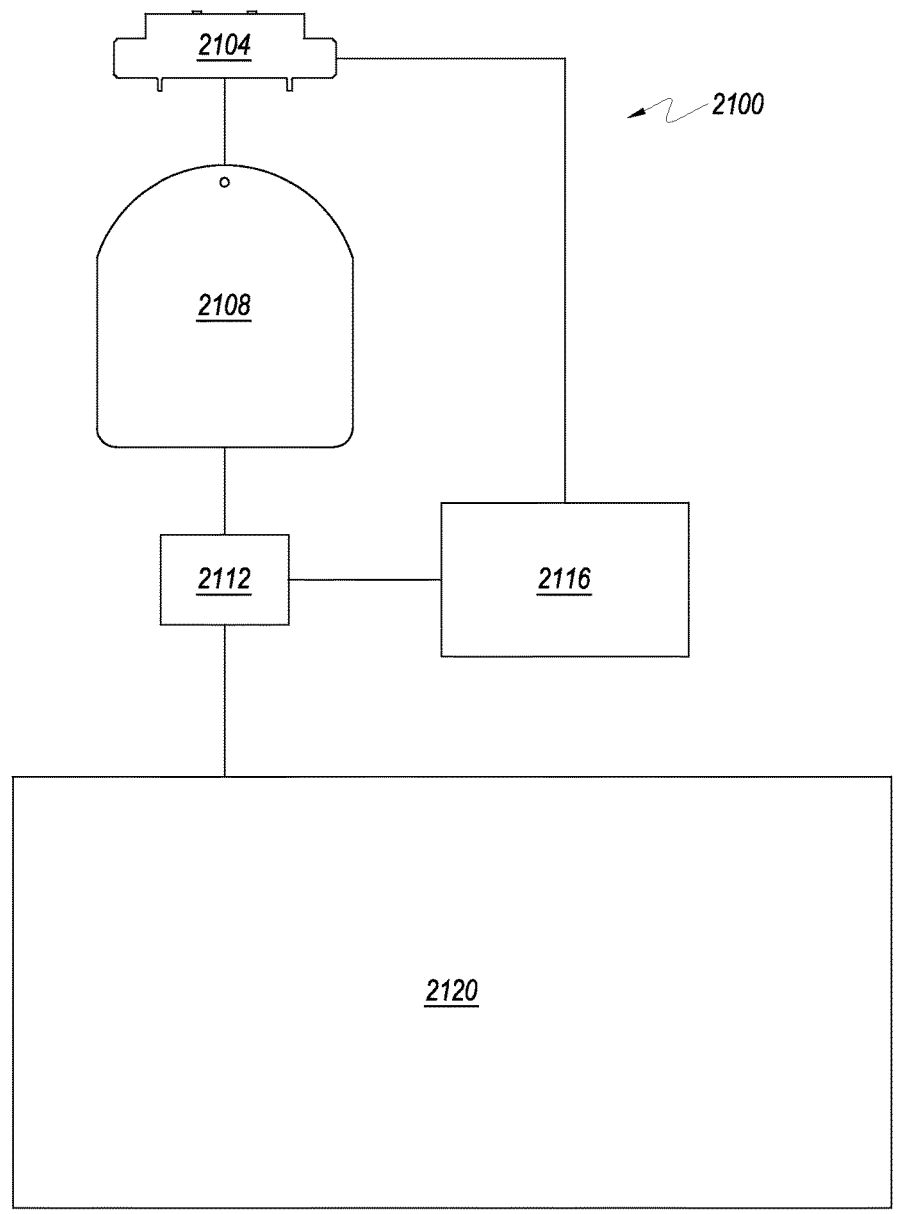
FIG. 21 illustrates a block diagram of an embodiment of a cell expansion system that includes a flow rate measurement system according to an embodiment.

FIG. 21 illustrates a block diagram of an embodiment of a system 2100 that includes a flow rate measurement system 2104 according to an embodiment. As illustrated in FIG. 21, in addition to flow rate measurement system 2104, fluid delivery system 2104 may include a fluid source 2108, such as a bag of fluid, a pump 2112, and a processor/controller 2116. Furthermore, system 2100 may include a fluid circulation system 2120 that includes various, flow path(s), growth chamber(s), gas transfer module(s), pump(s), fluid source(s), valve(s) etc. In one embodiment, a cell expansion system may comprise a part, or all of system 2120, including various, flow path(s), growth chamber(s), gas transfer module(s), pump(s), fluid source(s), valve(s) etc. One embodiment of a cell expansion system is described below with respect to FIG. 22.

In embodiments, system 2100 provides for delivering fluid as part of a cell expansion system(s) at consistent and accurate rates. For example, fluid may be delivered into an intracapillary or an extracapillary flow path of a hollow fiber membrane (e.g., cell growth chamber) where cells are grown (see FIG. 22 and description below). In embodiments, pump 2112 may be controlled to provide fluid at actual flow rates that may be maintained within about +/−5 percent over flow rates that range from about 0.025 milliliters per minute (ml/min) to about 1500 ml/min. The actual flow rate may, in other embodiments, be maintained within about +/−5 percent over flow rates that range from about 0.1 ml/min to about 1000 ml/min. In yet other embodiments, the actual flow rate may be maintained within about +/−5 percent over flow rates that range from about 0.1 ml/min to about 500 ml/min. Additionally, fluid volumes delivered by pump 2112 may range from about 0.05 milliliters (ml) to about 2000 ml, such as about 0.1 ml to about 500 ml.

Figure 22:
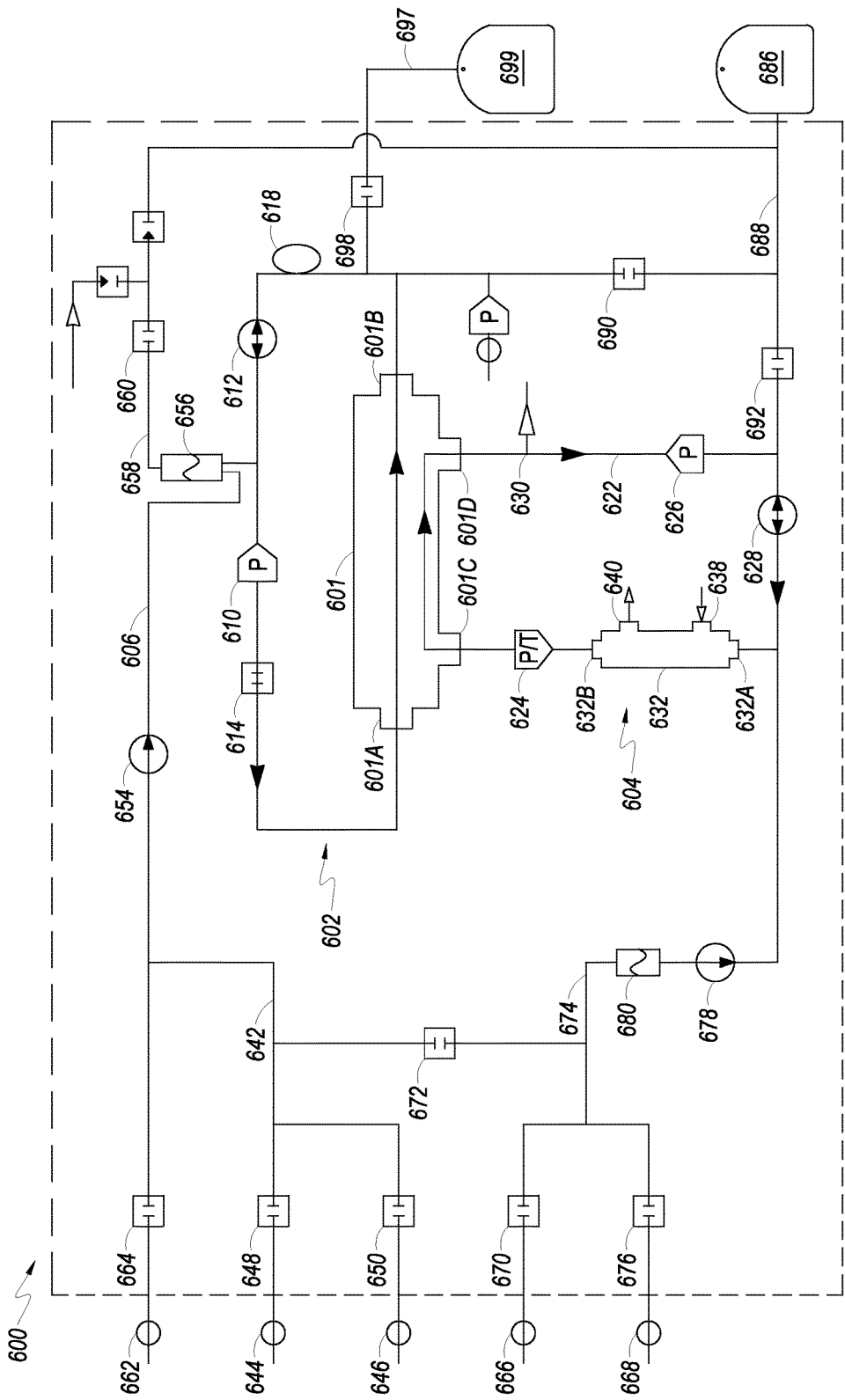
FIG. 22 illustrates a schematic of a cell expansion system that may utilize a flow rate measuring system according to an embodiment.

FIG. 22 illustrates a schematic of a cell expansion system (CES 600) that may be used with a flow rate measuring system (e.g., 100, 200, 2000, or 2104) according to an embodiment. In embodiments, CES 600 may comprise part, or all, of a fluid circulation system, such as system 2120 (FIG. 21).

CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 601B. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 601B may be used as an inlet in the reverse direction. Media entering the IC loop may enter through valve 614. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes bubbles from media in the CES 600. In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the second fluid inlet path 674.

In some embodiments, pumps 654 and 678 may be connected to one or more fluid flow rate measuring system(s) (e.g., system 100, 200, 2000, and/or 2104) and one or more processors for controlling the speed of the pumps. For example, embodiments may provide for one or more fluid flow measuring system(s) at each of attachment points 662, 644, 646, 666, and 668. The fluid flow measuring system(s) may be connected to a processor that is also connected to pumps 654 and 678. The processor may take information from fluid flow measuring system and determine fluid flow rates, which may result in changing of pump speeds of pumps 654 and 678.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699. Various components of the CES 600 may be contained or housed within a machine or housing, such as a cell expansion machine 2304 (FIG. 23) described below, wherein the machine maintains cells and media at a predetermined temperature.

Figure 23:
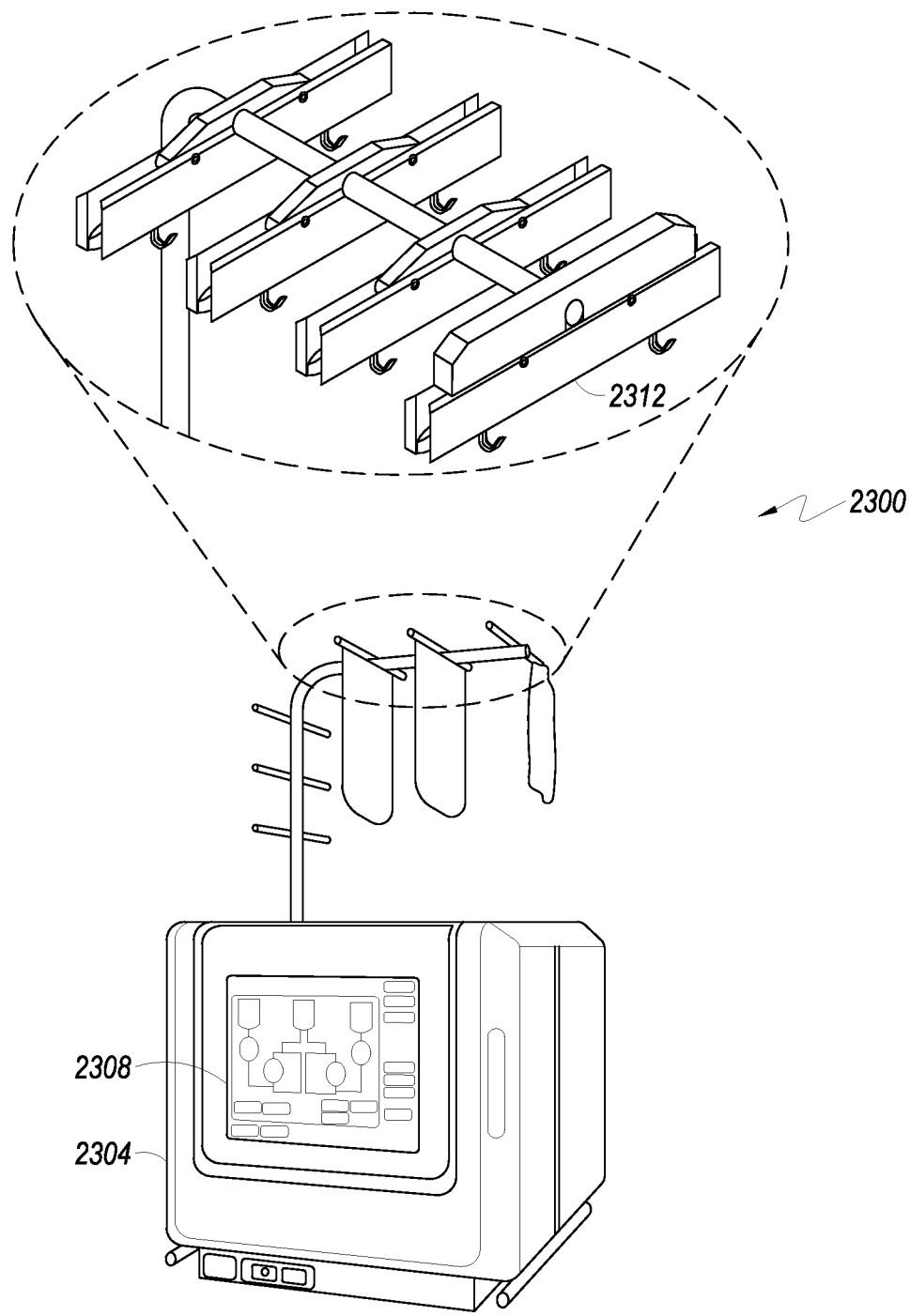
FIG. 23 illustrates an embodiment of a system that may include a flow rate measuring system according to an embodiment.

FIG. 23 illustrates a system 2300 that includes a cell expansion machine 2304 and at least one flow rate measuring system 2312. In embodiments, cell expansion machine 2304 houses components of a cell expansion system, such as the components of CES 600 described with respect to FIG. 22. Machine 2304 in embodiments, maintains components of a cell expansion system at a controlled temperature.

Machine 2304 may also include, inter alia, a computer system including one or more processors for controlling operation of the system 2300 and receiving information from flow rate measuring system 2312. Machine 2304 may also include input/output devices connected to the computer system, such as touch sensitive display 2308 for interfacing with an operator.

Figure 24:
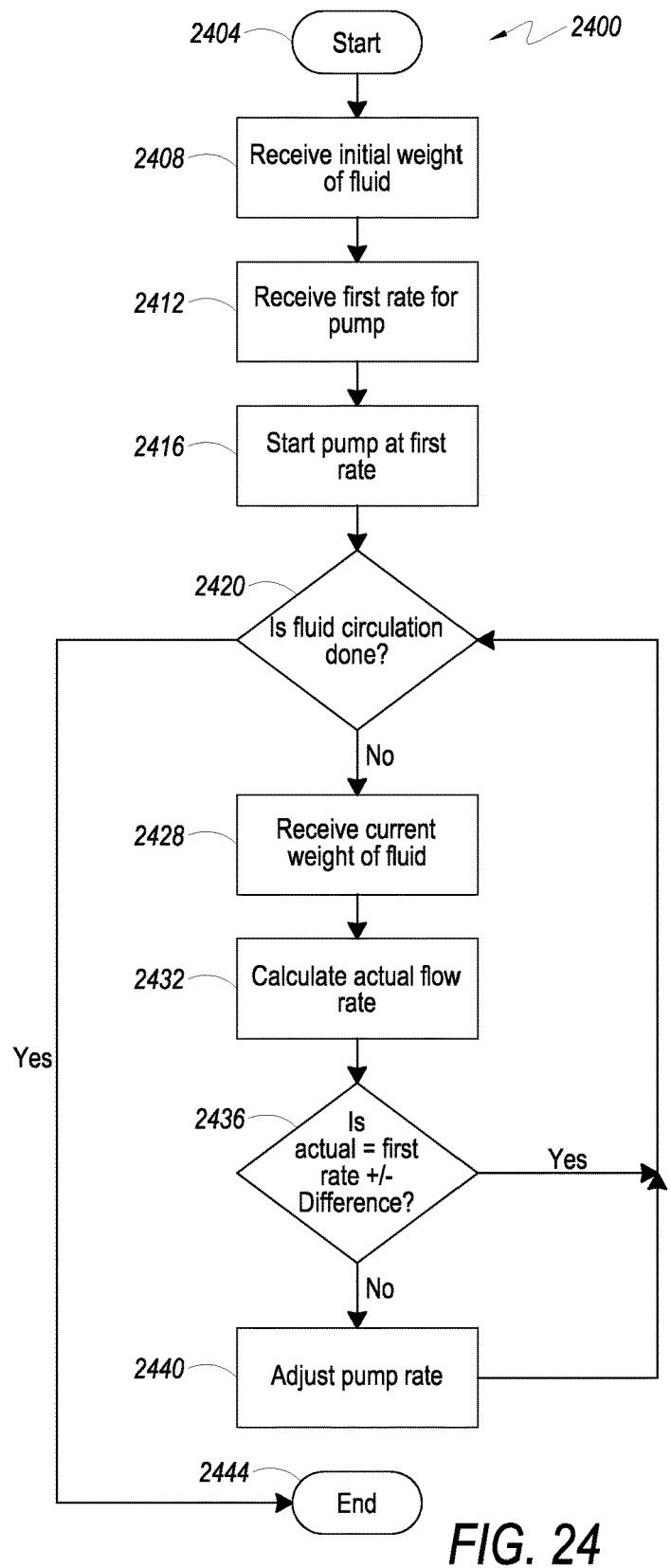
FIG. 24 illustrates a flow chart showing a method of controlling flow of fluid into a cell expansion system according to an embodiment.

FIG. 24 illustrates flow 2400 that may be performed in embodiments to control fluid input into a system such as a cell expansion system. Although specific devices may be described below for performing steps in flow 2400, embodiments are not limited thereto. For example, some steps may be described as performed by a processor, which may execute steps based on software provided as processor executable instructions. This is done merely for illustrative purposes, and flow 2400 is not limited to being performed by any specific device.

Flow 2400 starts at step 2404 and proceeds to step 2408 where an initial weight of fluid is received. In embodiments, a processor may receive the initial weight from a weighing device that may be part of a flow rate measuring system, such as a load cell or weight measuring device (e.g., 112A, 112B, 2012A, and 2012B).

In some embodiments, step 2404 may be preceded by some calibration steps. As one example, the weighing device may be zeroed. That is, the weighing device may be set to zero, prior to any fluid being connected to the weighing device.

Flow 2400 proceeds from step 2408 to step 2412 where a first rate for a pump may be received. The first rate may be in some embodiments received by a processor from an operator. For example, an operator may utilize a touch sensitive display for entering the first rate.

From step 2412, flow 2400 passes to 2416 where a pump is started at a first rate. After step 2416 a determination is made at 2420 as to whether the circulation of fluid is done because for example a predetermined time period has passed or a particular volume of fluid has been pumped. In embodiments, flow 2400 may be used during the pumping of a predetermined volume of fluid, which may range from about 0.05 ml to about 2000 ml, such as about 0.1 ml to about 500 ml. If a determination is made at 2420 that the circulation is done, flow 2400 ends at 2444.

If a determination is made at 2420 that the fluid circulation is not done, flow 2400 passes to step 2428 where a current weight of the fluid is received. As described above, in embodiments a processor may receive the current weight from a weighing device that may be part of a flow rate measuring system, such as a load cell (e.g., load cells 112A, 1126, 2012A, and 2012B).

At step 2432, the actual flow rate is calculated. As may be appreciated, step 2432 may involve a number of sub-steps, such as determining the changes from the initial weight to the current weight and determining a period of time that has passed between steps 2416 and 2428. In determining the actual flow rate at step 2432, the density of the fluid may also be used.

Step 2432 may involve the use of various algorithms to determine the actual flow rates. In one embodiment, the density of the fluid may be previously known. For example, if the solution comprises water, it may have a density of about 1 gram per liter (g/l). Step 2432 may therefore involve using the current weight received at step 2428 and subtracting the current weight from a previous weight to determine the weight of fluid that has been delivered in the period of time, which is recorded and/or calculated. Using the subtracted weight and the known density of the volume of fluid delivered during the period of time may be determined. A flow rate can then be determined by using the volume and the length of the period of time.

After step 2432, a determination is made at 2436 whether the actual flow rate is within some predetermined acceptable difference of the first flow rate. The predetermined acceptable difference may be some predetermined value, some non-limiting examples including, +/−0.025 milliliters per minute (ml/min), +/−0.05 ml/min, +/−1.0 ml/min, +/−2 ml/min, +/−3 ml/min, +/−4 ml/min, or even +/−5 ml/min. Alternatively, the predetermined acceptable difference may be a percentage such as about +/−5 percent, about +/−4 percent, about +/−3 percent, or even a bout +/−1 percent.

If a determination is made at 2436 that the actual flow rate is within the predetermined acceptable difference, flow 2400 passes back to 2420. If a determination is made at 2436 that the actual flow rate is not within the predetermined acceptable difference, flow passes to step 2440 where the first pump rate is adjusted. Depending on whether the actual pump rate calculated at 2432 is higher or lower than the first pump rate, the pump rate may be reduced or increased.

After the pump is adjusted at step 2440, flow 2400 passes back to 2420. If at 2420 a determination is made that the fluid circulation is not done, flow 2400 proceeds through steps 2428, 2432, 2436, and 2440. In embodiments, these steps provide for maintaining the actual flow rate (by controlling the speed of a pump) to within a predetermined difference of a set flow rate, i.e., the rate received at step 2412. That is, steps 2428, 2432, 2436, and 2440 are performed to maintain the actual flow rate at a rate received at step 2412. In embodiments, the actual flow rate may be maintained within at least about +/−5 percent over flow rates that range from about 0.025 milliliters per minute (ml/min) to about 1500 ml/min. The actual flow rate may, in other embodiments, be maintained within at least about +/−5 percent over flow rates that range from about 0.1 ml/min to about 1000 ml/min. In yet other embodiments, the actual flow rate may be maintained within at least about +/−5 percent over flow rates that range from about 0.1 ml/min to about 500 ml/min.

In other embodiments, the actual flow rate may be maintained within about +/−5 percent of a flow rate that may be about 0.1 milliliters per minute (ml/min), that may be about 1 ml/min, that may be about 8 ml/min, that may be about 10 ml/min, that may be about 50 ml/min, that may be about 100 ml/min, that may be about 150 ml/min, that may be about 200 ml/min, that may be about 350 ml/min, or that may be about 500 ml/min.

Referring back to FIG. 24, if at decision 2420 a determination is made that the fluid circulation is done, flow 2400 ends at 2444.

Figure 25:
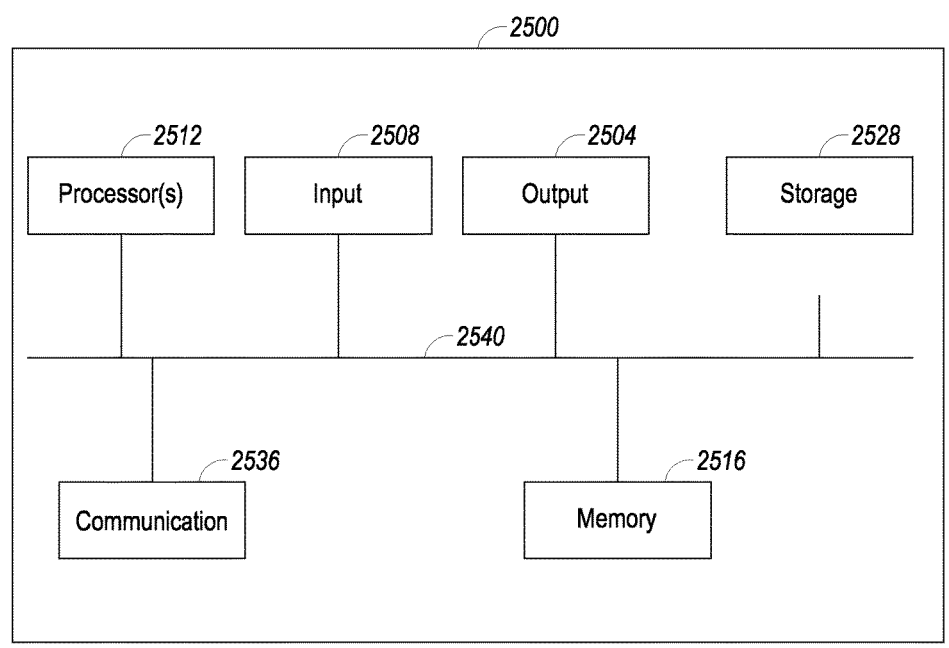
FIG. 25 illustrates components of a computing system that may be used to implement embodiments.

FIG. 25 illustrates example components of a basic computer system 2500 upon which embodiments may be implemented. Computer system 2500 includes output device(s) 2504, and input device(s) 2508. Output device(s) 2504 may include, among other things, one or more displays, including CRT, LCD, and/or plasma displays. Output device(s) 2504 may also include printers, speakers etc. Input device(s) 2508 may include, without limitation, a keyboard, touch input devices, a mouse, voice input device, scanners, etc. Computer system 2500 may include devices that are both input/output devices such as touch sensitive displays.

Basic computer system 2500 may also include one or more processor(s) 2512 and memory 2516, according to embodiments of the present invention. In embodiments, the processor(s) 2512 may be a general purpose processor(s) operable to execute processor executable instructions stored in memory 2516. Processor(s) 2512 may include a single processor or multiple processors, according to embodiments. Further, in embodiments, each processor may be a single core or a multi-core processor, having one or more cores to read and execute separate instructions. The processor(s) 2512 may include, in embodiments, general purpose processors, application specific integrated circuits (ASICs), field programmable gate arrays (FPGAs), and other integrated circuits.

The memory 2516 may include any tangible storage medium for short-term or long-term storage of data and/or processor executable instructions. The memory 2516 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc.

Storage 2528 may be any long-term data storage device or component. Storage 2528 may include one or more of the devices described above with respect to memory 2516. Storage 2528 may be permanent or removable.

Computer system 2500 also includes communication devices 2536. Devices 2536 allow system 2500 to communicate over networks, e.g., wide area networks, local area networks, storage area networks, etc., and may include a number of devices such as modems, hubs, network interface cards, wireless network interface cards, routers, switches, bridges, gateways, wireless access points, etc.

The components of computer system 2500 are shown in FIG. 25 as connected by system bus 2540. It is noted, however, that in other embodiments, the components of system 2500 may be connected using more than a single bus. In embodiments, 2116 (FIG. 21) or system 2300 (FIG. 23) may include aspects of computer system 2500.

It will be apparent to those skilled in the art that various modifications and variations can be made to the methods and structure of the present invention without departing from its scope. Thus it should be understood that the invention is not be limited to the specific examples given. Rather, the invention is intended to cover modifications and variations within the scope of the following claims and their equivalents.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A cell expansion system comprising:
  a hollow fiber membrane in a cell growth chamber;
  a flow rate measuring system comprising:
    a first weight measuring device adapted to weigh a container of fluid;
    a holding assembly adapted to connect the container of fluid to the weight measurement device;
  a pump adapted to move the fluid from the container of fluid into the hollow fiber membrane at a pump rate; and
  at least one processor connected to the pump, wherein the at least one processor is also connected to the flow rate measuring system and wherein the at least one processor:
    receives an initial weight of the fluid from the first weight measuring device;
    receives a current weight of the fluid from the first weight measuring device;
    determines a difference between the initial weight of the fluid and the current weight of the fluid; and
    using the difference between the initial weight of the fluid and the current weight of the fluid, a period of time, and a density of the fluid, determines an actual flow rate of fluid into the hollow fiber membrane; and
    adjusts the pump rate when the difference between the actual flow rate and a predetermined flow rate is greater than about 5 percent.

2. The system of claim 1, wherein the first weight measuring device comprises a load cell.

3. The system of claim 2, wherein the flow rate measuring system comprises a balance bar and the first weight measuring device is connected to a first channel of the balance bar and a second load cell is connected to a second channel of the balance bar.

4. The system of claim 1, wherein the predetermined flow rate ranges from about 0.1 milliliters per minute to about 500 milliliters per minute.

5. A method of controlling fluid input into hollow fibers in a cell growth chamber of a cell expansion system, the method comprising:
  receiving, by at least one processor, an initial weight of a fluid for pumping into hollow fibers in a growth chamber of a cell expansion system;
  receiving, by the at least one processor, a first pump flow rate;
  starting a pump to pump the fluid into the hollow fibers at the first pump flow rate;
  receiving, by the at least one processor, a current weight of the fluid;
  calculating, by the at least one processor, an actual pump flow rate using the difference between the initial weight of the fluid and the current weight of the fluid, density of the fluid, and a period of time between taking the initial weight of the fluid and the current weight of the fluid;
  determining, by the at least one processor, that the actual flow pump rate differs from the first pump flow rate by more than about 5 percent; and
  adjusting the first pump flow rate based on the determining.

6. The method of claim 5, wherein the current weight is received from a load cell.

7. The method of claim 6, wherein the first pump rate is between about 0.1 milliliters per minute and about 500 milliliters per minute.

* * * * *